(12) United States Patent
Huang et al.

(10) Patent No.: US 9,980,990 B2
(45) Date of Patent: May 29, 2018

(54) LACTOBACILLUS STRAIN, COMPOSITION AND USE THEREOF FOR TREATING SYNDROMES AND RELATED COMPLICATIONS OF AUTOIMMUNE DISEASES

(71) Applicant: GenMont Biotech Incorporation, Tainan (TW)

(72) Inventors: Chih-Yang Huang, Taichung (TW); Wei-Wen Kuo, Taichung (TW); Bor-Show Tzang, Taichung (TW); Yi-Hsing Chen, Tainan (TW)

(73) Assignee: GenMont Biotech Incorporation, Tainan (TW)

( * ) Notice: Subject to any disclaimer, the term of this patent is extended or adjusted under 35 U.S.C. 154(b) by 213 days.

(21) Appl. No.: 14/623,527

(22) Filed: Feb. 17, 2015

(65) Prior Publication Data
US 2015/0238548 A1 Aug. 27, 2015

(30) Foreign Application Priority Data
Feb. 21, 2014 (TW) ............... 103105864 A (51) Int. Cl.
*C12N 1/20* (2006.01)
*A61K 35/747* (2015.01)
*C12R 1/225* (2006.01)

(52) U.S. Cl.
CPC .............. *A61K 35/747* (2013.01); *C12N 1/20* (2013.01); *C12R 1/225* (2013.01)

(58) Field of Classification Search
None
See application file for complete search history.

(56) References Cited

U.S. PATENT DOCUMENTS

| 9,301,984 B2 | 4/2016 | Chen et al. |
| 2009/0196921 A1 | 8/2009 | Ebel et al. |
| 2011/0300117 A1 | 12/2011 | Leu et al. |
| 2012/0263695 A1 | 10/2012 | Schrezenmeir et al. |

FOREIGN PATENT DOCUMENTS

| CN | 1696281 A | 11/2005 |
| CN | 101575582 A | 11/2009 |
| CN | 102100704 A | 6/2011 |
| CN | 102115721 A | 7/2011 |
| CN | 102935092 A | 2/2013 |
| EP | 1481681 A1 | 12/2004 |
| EP | 2392340 A1 | 12/2011 |
| JP | 2009057346 A | 3/2009 |
| JP | 2012-149026 A * | 8/2012 |
| TW | I284149 | 7/2007 |
| TW | I340021 | 4/2011 |
| TW | I346554 | 8/2011 |
| TW | I355939 | 1/2012 |
| TW | 201210603 A | 3/2012 |
| TW | I406665 B1 | 9/2013 |
| WO | 01/11077 A2 | 2/2001 |
| WO | 0111334 A2 | 2/2001 |
| WO | 2006/102536 A2 | 9/2006 |
| WO | 2007/040446 A1 | 4/2007 |
| WO | 2009027753 A1 | 3/2009 |

OTHER PUBLICATIONS

JP02012149026A, Machine Translation, Aug. 2012.*
"How dose lupus affect the heart and cirsulation," Lupus Foundation of America, Aug. 11, 2013.
"How dose lupus affect the gastrointestinal system," Lupus Foundation of America, Jul. 12, 2013.
M. Salmon et al., "The role of apoptosis in systemic lups erythematosus," Rheumatology 1999;38:1177-1183.
Tom Van Belle et al. "Type 1 Diabetes: Etiology, Immunology, and Therapeutic Strategies", Physiological Reviews, vol. 91, No. 1, 2011, pp. 79-118.
Harman et al. "Prevalence and natural history of histologically proven chronic liver disease in a longitudinal cohort of patients with type 1 diabetes", Hepatology, vol. 56, No. 4, Oct. 2012, p. 881A-882A, #1467.
Manirarora, Jean Nepomuscene "Manipulating antigen -presenting cell function to restore immune regulation in autoimmune-prone mice", ProQuest Dissertations Publishing, 2008, pp. 111, 113-115.
Pascale Alard et al., Abstract of "Probiotics control lupus progression via induction of regulatory cells and IL-10 production", http://www.jimmunol.org/content/182/1_Supplement/50.30, Apr. 2009.
Hermelijn H. Smits, PhD et al., "Selective probiotic bacteria induce IL-10-producing regulatory T cells in vitro by modulating dendritic cell function through dendritic cell-specific intercellular adhesion molecule 3-grabbing nonintegrin", J Allergy Clin Immunol, vol. 115, No. 6, Jun. 2005, pp. 1260-1267.
Matteo Bellone, "Autoimmune Disease: Pathogenesis", Encyclopedia of Life Sciences, published online Sep. 2015.

* cited by examiner

Primary Examiner — Irene Marx
(74) Attorney, Agent, or Firm — CKC & Partners Co., Ltd.

(57) ABSTRACT

The present invention is related to a *Lactobacillus* strain, composition and use thereof for treating autoimmune disease and related complications. The composition comprises at least one isolate of *Lactobacillus paracasei* strain GMNL-32, *L. reuteri* strain GMNL-89 or *L. reuteri* strain GMNL-263, and a pharmaceutical carrier, for treating syndromes and related complications of the autoimmune diseases.

3 Claims, 11 Drawing Sheets

Control

Fig. 10A

GMNL-32

Fig. 10B

GMNL-89

Fig. 10C

GMNL-263

Fig. 10D

LACTOBACILLUS STRAIN, COMPOSITION AND USE THEREOF FOR TREATING SYNDROMES AND RELATED COMPLICATIONS OF AUTOIMMUNE DISEASES

RELATED APPLICATIONS

This application claims priority to Taiwan Application Serial Number 103105864, filed Feb. 21, 2014, which is herein incorporated by reference.

BACKGROUND

Field of Invention

The disclosure relates to a *Lactobacillus* strain and an application thereof. More particularly, the disclosure relates to a *Lactobacillus* strain for treating syndromes and related complications of autoimmune diseases and a composition thereof.

Description of Related Art

An autoimmune disease is a disease that a human body's immune system attacks normal cells of his body. Such patient has weaker normal immunity but stronger aberrant immunity. The "aberrant immunity" refers to the immune system that recognizes the normal cells of its own body as foreign virus or bacteria and targets the normal cells for attacking and clearing them out of the body. The normal immune system of a human body provides a physically protective mechanism to target foreign antigens and abnormal cells, such as tumor cells, for attacking and clearing them out of the human body. However, sometimes the immune system may produce some antibodies against the normal cells or normal cellular components. Therefore, some aberrant excessive inflammation or tissue damage may cause diseases and adversely effect health.

Common autoimmune diseases include coeliac disease, type 1 diabetes mellitus, systemic lupus erythematosus (SLE), Sjögren's syndrome, multiple sclerosis (MS), Hashimoto's thyroiditis, Graves' disease, idiopathic thrombocytopenic purpura, rheumatoid arthritis (RA), aplastic anemia, polymyositis and dermatomyositis, as well as scleroderma.

Among those, systemic lupus erythematosus (SLE) is a chronic systemic autoimmune disease, in which the body's immune system turns against all organs or tissues of the body itself, including skin, joints, heart, blood vessels, liver, kidneys, brain and nervous system. In general, the course of SLE is alternatively aggravated and released, and the onset is usually unpredictable. This disease, which may occur in people of any age, most commonly occurs in young women, and 90% of SLE patients are women. The signs and symptoms of SLE vary greatly in different individuals. When onset of SLE, some patients have severe symptoms with the important organs such as the central nervous system, kidney, heart and so on, whereas some other patient only have mildly joint symptoms during life. As for the incidence, above 90% of the SLE patients have joint pain or arthritis, 70% to 80% of the SLE patients have skin erythema or discoid erythema, 40% to 50% of the SLE patients have pleurisy or pericarditis, 40% to 50% of the SLE patients have lupus nephritis, 20% to 60% of the SLE patients have central nervous system violations, and 20% of the SLE patients have thrombocytopenia.

At present, the cause of the SLE is still unclear, but it is believed that SLE is related to genes, immunodeficiency, viral infections, UV, and drugs. Recent studies have found that, SLE patients have much higher incidence of liver abnormalities (such as hepatomegaly, splenomegaly, jaundice, abnormal liver function, abnormal liver enzymes and so on) and the cardiovascular disease (CVD, such as myocardial infarction (MI)) than normal people, and the atherosclerosis is also highly associated with SLE. Some studies with animal models reveal that significant inflammation and apoptosis of liver and heart occur in SLE mice.

SLE is currently incurable, but its symptoms can be treated. Medicines are important to the treatment of SLE. Physicians prescribe mediation to treat a SLE patient depending on symptoms, the different organ injuries and different severities. Common medications used to treat SLE manifestations include the followings.

(1) Non-Steroidal Anti-Inflammatory Drugs (NSAIDs):
NSAIDs can be used to treat arthritis, pleurisy, and other lighter inflammatory symptoms. Gastrointestinal side effects are the major problem of NSAIDs. Fortunately, a new generation of selective inhibitor of type II cyclooxygenase (COX-2) has been commercially marketed, and it causes much less gastrointestinal side effect than the traditional NSAIDs.

(2) Antimalarial Drugs:
Most commonly antimalarial drug is hydroxychloroquine (or the brand name of Plaquenil). The clinical uses show that the antimalarial drugs have a fairly good efficacy on the treatment of skin symptoms, arthritis, and other mild systemic symptoms of SLE patients. The antimalarial drugs also can decrease the recurrence of SLE.

(3) Cortisol:
Cortisol is generally known as the "American panacea" or "steroids." Cortisol is the most important drugs for treating SLE. Higher dose of steroids should be used in severe conditions of internal organ damages such as lupus nephritis, nervous system lupus, lupus pneumonitis, hemolytic anemia, or thrombocytopenia and so on. The physician also considers supplying an intravenous pulse steroid therapy with high dose of steroids, so that the condition is controlled as soon as possible, and the dose of the steroids is then gradually decreased to a minimal level when clinically well controlled.

(4) Immunosuppressing Drugs:
Immunosuppressing drugs are mainly used to inhibit the activity of the immune system, so as to achieve good control and efficacy of the autoimmune diseases. Immunosuppressing drugs are usually used with steroids, so as to decrease the doses of the steroids and to effectively control the stubborn disease. Common immunosuppressing drugs include azathioprine (Imuran®), cyclophosphamide (Endoxan®), cyclosporine, methotrexate (MTX) and so on.

Probiotics or probiotic bacteria generally refer to live microorganisms originating from human bodies and beneficial to intestinal tract health, or some microorganisms supplied from outside sources and beneficial to human health, for example, lactic acid bacteria (LAB) and some yeasts. 70% of human immune system is located in the digestive tract. As early as the late nineteenth century, Russia scientists have observed that probiotics have health effect to human body. Previous studies have shown that more than ⅓ SLE patients have gastrointestinal symptoms, and 10% SLE patients have gastrointestinal pathological changes at the first onset. It is currently known that probiotics are capable of restoring intestinal flora balance, stimulating mucosal immunity, improving gastrointestinal discomfort and improving urogenital flora.

Recently, some studies attempt to treat SLE with *Lactobacillus*. The obtained results show that the single *Lacto-*

*bacillus* strain can promote the production of anti-inflammatory cytokines such as interleukin-10 (IL-10) and tumor necrosis factor-α (TNF-α), to treat the autoimmune diseases such as SLE.

However, the aforementioned studies seldom investigated whether LABs is used to treat the symptoms of the autoimmune diseases (such as SLE) and their complications (such as cardiac and hepatic disease), and did not propose any regulatory mechanism that LABs may be involved in SLE treatments.

Side effects often occur in drugs for the treatment of autoimmune diseases (such as SLE), and patients with such chronic diseases must be treated and controlled for a long time. Therefore, there is a need to use native *Lactobacillus* strains to develop products that are capable of treating symptoms and complications of autoimmune diseases, so as to achieve the improvement, control, remedy, or prevention of the patients with the symptoms and complications of autoimmune diseases, as well as the development of other applications of *Lactobacillus* strains.

SUMMARY

Accordingly, an aspect of the invention provides an isolated strain of *Lactobacillus* species for treating a syndrome and a complication of an autoimmune disease.

Another aspect of the invention provides a lactic acid bacteria (LAB) strain used for preparation of a medical composition for treating a syndrome of an autoimmune disease and its complication.

Yet another aspect of the present invention provides a LAB-containing composition containing the aforementioned LAB strain, for treat a syndrome of an autoimmune disease and its related complication via oral administration.

In light of foregoing, an isolated strain of *Lactobacillus* for treating a syndrome and a complication of an autoimmune disease is provided. The isolated strain includes but is not limited to at least one of *Lactobacillus paracasei* strain GMNL-32 (the accession numbers of BCRC 910220 and CCTCC M 204012), *L. reuteri* strain GMNL-89 (the accession numbers of BCRC 910340 and CCTCC M 207154), *L. reuteri* strain GMNL-263 (the accession numbers of BCRC 910452 and CCTCC M 209263), or any combinations thereof. The aforementioned *Lactobacillus* strain are deposited in Food Industry Research and Development Institute (FIRDI), Hsin-Chu, Taiwan, as well as China Center for Type Culture Collection (CCTCC), Wuhan University, Wuhan 430072, People's Republic of China.

According to another aspect, a lactic acid bacteria (LAB) strain used for preparation of a medical composition for treating a syndrome and a complication of an autoimmune disease is provided. The medical composition comprises an effective amount of the LAB strain and a pharmaceutically acceptable carrier, and the LAB strain can include but be not limited to at least one isolated strain of the aforementioned *Lactobacillus* species.

According to yet another aspect, a LAB-containing composition is provided. The LAB-containing composition comprises an effective amount of a LAB strain and an edible material. The LAB strain is at least one of the isolated strains of the aforementioned *Lactobacillus* species.

According to some embodiments, when the LAB strain is used for preparation of the medical composition for treating the syndrome and the complication of the autoimmune disease, the LAB strain is live and/or inactivated. Moreover, the aforementioned medical composition further comprises a pharmaceutically acceptable carrier, which can use any conventional carrier rather than being recited in detail. In addition, the aforementioned LAB strain can be applied to any form of easy to use in daily life, for example, healthy food, additives, medical compositions, dietary supplement, food and so on. In other examples, the aforementioned LAB strain can be produced in the freeze-dried form, and it can further include other ingredients such as glucose, maltodextrin, baby milk, fructo-oligosaccharides, magnesium stearate, yogurt spices, other uncertain remains unseparated therefrom or any combinations thereof. Furthermore, the aforementioned LAB strain may be used to specifically inhibit activities of matrix metallopeptidase 9 (MMP-9), C-reactive protein (CRP), interleukin-1β (IL-1β), tumor necrosis factor-α (TNF-α), IL-6 and inducible NO synthase (iNOS).

According to an embodiment, the aforementioned autoimmune disease can be systemic lupus erythematosus.

In light of the foregoing, the isolated strain of the *Lactobacillus* species of the present invention, the medical composition containing the same, and the LAB-containing composition, can be administrated orally to specifically inhibit activities of MMP-9, CRP, IL-1β, TNF-α, IL-6, iNOS to a subject having an autoimmune disease, for treating the syndrome and the complication (such as cardiac and hepatic disease) of the autoimmune disease, thereby developing other application fields of the LAB strains.

These and other features, aspects, and advantages of the present invention will become better understood with reference to the following description and appended claims.

BRIEF DESCRIPTION OF THE DRAWING

The invention can be more fully understood by reading the following detailed description of the embodiment, with reference made to the accompanying drawings as follows.

DETAILED DESCRIPTION

In light of forgoing, this invention provides an isolated strain of *Lactobacillus* species for treating autoimmune disease and complications thereof, a medical composition comprising lactic acid bacteria (LAB) and a LAB-containing composition for treating autoimmune disease and complications thereof. The isolated strain of the *Lactobacillus* species comprises at least one *Lactobacillus* strain, and can be administered orally to treat the syndrome and complication (such as cardiac and hepatic disease) of the autoimmune disease.

The "isolated strain of the *Lactobacillus* species" recited herein includes but is not limited to *Lactobacillus paracasei* strain GMNL-32, *L. reuteri* strain GMNL-89, *L. reuteri* strain GMNL-263 or any combinations thereof. The *L. paracasei* strain GMNL-32 has been deposited in Bioresource Collection and Research Center (BCRC) of Food Industry Research and Development Institute (FIRDI), Hsin-Chu, Taiwan on Mar. 19, 2003 under the accession number of BCRC 910220, and also deposited in China Center for Type Culture Collection (CCTCC), Wuhan University, Wuhan 430072, People's Republic of China on Feb. 19, 2004 under the accession number of CCTCC M 204012. The *L. reuteri* strain GMNL-89 has been deposited in BCRC of FIRDI on Nov. 14, 2006 under the accession number of BCRC 910340, and also deposited in CCTCC on Nov. 19, 2007 under the accession number of CCTCC M 207154. The *L. reuteri* strain GMNL-263 has been deposited in BCRC of FIRDI on Nov. 6, 2009 under the accession number of BCRC 910452, and also deposited in CCTCC on Nov. 13, 2009 under the accession number of CCTCC M 209263.

The aforementioned *L paracasei* strain GMNL-32 (also called as GM-080) is a disclosed strain (the accession numbers of BCRC 910220 and CCTCC M 204012). The related strain characteristics have been disclosed in TW I284149 titled as "novel microorganism strain GMNL-32 of *Lactobacillus paracasei* for allergy diseases treatment", and TW 201210603 titled as "composition and use of probiotic strain GM-080 in treating cardiac inflammation and apoptosis", both of which are herein incorporated by reference.

The *L. reuteri* strain GMNL-89 is also a disclosed strain (the accession numbers of BCRC 910340 and CCTCC M 207154). The related strain characteristics have been disclosed in TW I340021 titled as "novel *Lactobacillus* strain, composition and use thereof for improving the syndrome of diabetes and complication thereof", and TW I346554 titled as "*Lactobacillus* isolates having anti-inflammatory activities and uses of the same", both of which are herein incorporated by reference.

The *L. reuteri* strain GMNL-263 is also a disclosed strain (the accession numbers of BCRC 910452 and CCTCC M 209263). The related strain characteristics have been disclosed in TW I340021 titled as "novel *Lactobacillus* strain, composition and use thereof for improving the syndrome of diabetes and complication thereof" and TW I355939 titled as "composition and use of probiotic strain GM-263 (ADR-1) in treating renal fibrosis in diabetes", both of which are herein incorporated by reference.

In general, the aforementioned LAB strains can be subjected to various available culturing methods to obtain the isolated strain. The "isolated strain" recited herein refers to a strain obtained from a pure culture of a single colony of the aforementioned LAB strain, which substantially does not contain other strains.

In application, when the LAB strain is used for preparation of the medical composition for treating the syndrome and the complication of the autoimmune disease, the LAB strain is live and/or inactivated. Moreover, the aforementioned medical composition further comprises a pharmaceutically acceptable carrier, which can use any conventional carrier rather than being recited in detail. In addition, the aforementioned LAB strain can be applied to any form of easy to use in daily life, for example, healthy food, additives, medical compositions, dietary supplement, food and so on. In other examples, the aforementioned LAB strain can be produced in the freeze-dried form, and it can further include an edible material such as glucose, maltodextrin, baby milk, fructo-oligosaccharides, magnesium stearate, yogurt spices, other uncertain remains unseparated therefrom or any combinations thereof. Furthermore, one or more pure culture of LAB strains are mixed well with a pharmaceutically acceptable carrier, so as to prepare a medical composition containing the aforementioned LAB strains. A formulation of the aforementioned medical composition can include but be not limited to a solution, a suspension solution, an emulsion, powder, a tablet, a pill, a syrup, a lozenge, a troche, a chewing gum, a thick slurry, a capsule or any combination thereof. The aforementioned medical composition is then analyzed by animal model, such as SLE mice. The results prove that the aforementioned medical composition can treat, alleviate, control, improve, and/or prevent the cardiac and hepatic disease and related complications caused by autoimmune diseases.

In detail, "the treatment and improvement of cardiac and hepatic disease and related complication of the autoimmune disease" recited herein refers to the aforementioned medical composition containing the above strains of *Lactobacillus* for continuously oral administration to a subject in a daily dosage of about $1 \times 10^6$ colony-forming unit per gram (CFU/g) to about $1 \times 10^{11}$ CFU/g for at least 12 weeks. Such medical composition is easy-to-use in the daily life of patients, and can treat, alleviate, control, improve, and/or prevent the hepatic disease-related protein expression caused by the autoimmune disease (such as SLE) in the animal body. For example, the aforementioned medical composition can specifically inhibit activities of MMP-9, CRP, IL-1β, TNF-α, IL-6 and iNOS. Also, the aforementioned medical composition can treat, alleviate, control, improve, and/or prevent cardiac disease-related syndromes caused by the autoimmune disease, so as to restore heart weight and reduce gap junctions between cardiac cells, for example.

Thereinafter, various applications of the LAB strains of the present invention will be described in more details referring to several exemplary embodiments below, while not intended to be limiting. Thus, one skilled in the art can easily ascertain the essential characteristics of the present invention and, without departing from the spirit and scope thereof, can make various changes and modifications of the invention to adapt it to various usages and conditions.

Example Embodiment 1: Establishment and Evaluation of Animal Model

1. Preparation of *Lactobacillus* Strains

*L. paracasei* strain GMNL-32 (the accession number of BCRC 910220), *L. reuteri* strain GMNL-89 (the accession number of BCRC 910340) and *L. reuteri* strain GMNL-263 (the accession number of BCRC 910452) were used to perform SLE animal experiments, for evaluating the effect of treating the cardiac and hepatic disease caused by SLE via oral administration.

The total dosages per day of the aforementioned three *Lactobacillus* strains were $1 \times 10^9$ CFU/g, respectively. The aforementioned three *Lactobacillus* strains were produced in the freeze-dried form, and included other ingredients such as glucose, maltodextrin, baby milk, fructo-oligosaccharides, magnesium stearate, yogurt spices, other uncertain remains unseparated therefrom or any combinations thereof.

2. Establishment of SLE Animal Testing Model

New Zealand Black/White F1 hybrid (NZB/W F1) female mice (Jackson Lab, U.S.A.) were exemplified to establish SLE animal testing model. First, SLE mice were randomly assigned to three experimental groups and one control group. Each group had 8 SLE mice of 14 weeks old. The SLE mice of the experimental groups were fed a diet with 1×10 CFU/g per mouse of various LAB strains including *Lactobacillus paracasei* strain GMNL-32, *L. reuteri* strain GMNL-89 or *L. reuteri* strain GMNL-263 respectively. The SLE mice of the control group were fed a basic diet replaced by deionized water having the same weight as the LAB strains.

The SLE mice were raised at ambient temperature controlled at 25±1° C., relative humidity at 65±5%. In addition, the SLE mice were maintained on a reverse 12 hours light-dark cycle. The SLE mice were provided with standard laboratory chow and water ad libitum. All experimental procedures were approved according to related guidelines for the management of the laboratory animals announced by National Health Research Institutes (NHRI), Taiwan.

All SLE mice were weighted after 12 weeks, and then sacrificed. The liver, heart and coronary artery were dissected and then washed by distilled water. The left and right atriums and ventricles were divided and separately weighted for subsequent analyses.

3. Extraction of Liver Tissue

The livers of the aforementioned SLE mice were respectively immersed in lysis buffer, and then 100 mg of liver tissue in 1 mL of the lysis buffer were homogenized for 1 minute, so as to dissolve hepatocytes and release the proteins in the hepatocytes. The aforementioned lysis buffer included 20 mM of tris(hydroxymethyl) aminomethane (Tris) solution, 2 mM of tris(hydroxymethyl) aminomethane (EDTA), 50 mM of 2-mercaptoethanol, 10% of glycerol, proteinase inhibitor (Roche) and phosphatase inhibitor cocktail (Sigma), and the pH value of the lysis buffer was 7.4. Next, the resultant homogenate was placed on ice for 10 minutes, and then centrifuged twice at 12000 g for 40 minutes. The supernatant was taken and stored at −80° C. for following assessments.

4. Western Blot

Hereinafter, electrophoresis and western blot were used to evaluate the effects of the three *Lactobacillus* strains on the treatment of the liver diseases caused by SLE.

The aforementioned supernatant were loaded into 10% sodium dodecyl sulfate-polyacrylamide gel electrophoresis (SDS-PAGE), and electrophoresed at a voltage of 85 volts for 3.5 hours. Next, the gel was equilibrated in 25 mM of Tris-HCl buffer (pH 8.3) containing 192 mM of glycine and 20% (v/v) of methanol for 15 minutes. The preparation of SDS-PAGE and related equipments were familiar with the artisan in this art of the present invention rather than being recited in detail herein.

The SDS-PAGE gel was then subjected to western blotting assay. In this Example, the kit of western blotting assay (such as Bio-Rad Scientific Instruments Transfer Unit) was used to transfer electrophoresed proteins to a transfer membrane, such as polyvinylidene difluoride (PVDF) membrane (0.45 m of pore size, Millipore, Bedford, Mass., U.S.A.) at a voltage of 85 volts for 2.5 hours. Next, the transfer membrane was incubated in a blocking solution containing 5% skim milk powder dissolved in TBS buffer (Tris-Base, NaCl, Tween-20, pH 7.4) at room temperature for 1 hour. Subsequently, the transfer membrane was incubated in a primary antibody diluted 500-fold in an antibody-binding buffer overnight at 4° C. Later, the transfer membrane was washed three times for 10 minutes each with TBS buffer. Afterwards, the transfer membrane was incubated in a secondary antibody diluted 500-fold in TBS buffer solution at 37° C. for 1 hour. Later, the transfer membrane was washed three times for 10 minutes each with TBS buffer. Finally, the immunoblotted proteins were visualized by a luminescence coloring agent such as an enhanced chemiluminescence (ECL) western blotting luminol reagent (Pierce Biotechnology Inc., Rockford, Ill., U.S.A.) and analyzed by a luminescence and fluorescence analyzing system (ImageQuant LAS-4000, GE Healthcare Life Sciences Inc., U.S.A.).

The aforementioned primary antibody included anti-CRP monoclonal antibody (Santa Cruz Biotechnology, Inc., Texas, U.S.A.), anti-IL-1β monoclonal antibody (Santa Cruz Biotechnology, Inc., Texas, U.S.A.), anti-TNF-α monoclonal antibody (Santa Cruz Biotechnology, Inc., Texas, U.S.A.), anti-IL-6 monoclonal antibody (Santa Cruz Biotechnology, Inc., Texas, U.S.A.), or anti-iNOS monoclonal antibody (Santa Cruz Biotechnology, Inc., Texas, U.S.A.). The aforementioned secondary antibody included goat anti-mouse IgG-HRP, goat anti-rabbit IgG-HRP, or donkey anti-goat IgG-HRP, all of which were purchased from Santa Cruz Biotechnology (Santa Cruz, Calif., U.S.A.) or Santa Cruz Biotechnology, Inc. (Texas, U.S.A.).

5. Gelatin Zymoaraphy Protease Assay

The aforementioned supernatant from liver was subjected to an MMP activity test. The aforementioned supernatant were loaded into 8% SDS-PAGE gel containing 0.1% gelatin, and electrophoresed at a voltage of 100-120 volts for 3-4 hours. Then, the gel was washed in 2.5% of Triton X-100 solution once or twice with shaking for 30 minutes to recover the function of the proteases. The preparation of the gelatin-SDS-PAGE gel and the related equipments were familiar with the artisan in this art of the present invention rather than being recited in detail herein.

Afterwards, the gelatin-SDS-PAGE gel was placed in a solution containing 40 mM of Tris-HCl (pH 8.0), 10 mM of $CaCl_2$, and 0.01% (w/v) of $NaN_3$, and then incubated at 37° C. for 16 hours. Next, the electrophoretic gel was stained by 0.25% (w/v) of Coomassie Brilliant Blue R-250 (Sigma-Aldrich Inc., U.S.A.) for 30 minutes, and then decolored by a decoloring solution containing 875 mL of deionized water ($dH_2O$), 50 mL of methanol, and 75 mL of acetic acid. The band intensities of serum MMP-9 (about 92 kDa) and serum MMP-2 (about 62 kDa) on the gelatin-SDS-PAGE gel were qualified by a commercial image analysis software/device such as a densitometer (Appraise, Beckman-Coulter, Brea, Calif., U.S.A.), so as to calculate the content ratio of MMP-9 to MMP-2 (MMP-9/MMP-2).

The data were all shown in mean±standard error of mean, and analyzed by SAS 9.1 software. Tukey-type multiple comparison test based on the studentized residuals was used to examine the statistical differences among individual groups. The symbol * in figures referred to significant difference ($p<0.05$) between the experimental groups and the control group.

6. Immunohistochemistry (IHC)

The tissue was embedded in an optimal cutting temperature (OCT) embedding agent and then cryosectioned to histological sections having a thickness of 5 μm by a commercial cryostat microtome. The histological sections were picked up on a glass that can be stored at −20° C. Next, histological sections were stained by Masson's trichrome stain (Sigma-Aldrich Inc., U.S.A.) or indirectly immunostained by anti-α-smooth muscle actin (α-SMA) antibody, for facilitating observation of changes in the cardiac tissue, cell morphology and cellular structure. The OCT-embedded blocks, histological sections, and Masson's trichrome staining were familiar with the artisan in this art of the present invention rather than being recited in detail herein.

Example 2: Evaluation of Efficacy of the LAB Strains to the Treatment of Liver Disease 1. Evaluation of the Influence of the LAB Strains on the Liver Weight of SLE Animal SLE mice of EXAMPLE 1 were respectively fed deionized water (the control group), the *L. paracasei* strain GMNL-32, the *L. reuteri* strain GMNL-89 and the *L. reuteri* strain GMNL-263. After 12 weeks, the liver weight (L) and body weight (B) were measured and listed in TABLE 1 as follows. Moreover, the liver-to-body weight ratios (L/B) were listed in TABLE 1 and FIG. 1.

TABLE 1

| | Group | | | |
|---|---|---|---|---|
| | Control | *L. paracasei* strain GMNL-32 | *L. reuteri* strain GMNL-89 | *L. reuteri* strain GMNL-263 |
| Liver weight (L) (mg) | 1549.283 ± 41.994 | 1881.587 ± 93.034 | 1543.271 ± 61.597 | 1649.314 ± 123.633 |
| Body weight (B) (g) | 39.169 ± 0.704 | 45.26314 ± 1.878 | 41.17843 ± 2.061 | 43.25257 ± 0.834 |
| Weight ratio of L/B | 39.503 ± 0.466 | 41.74273 ± 3.035 | 38.18335 ± 1.174 | 36.03054 ± 1.236 |

Figure 1:
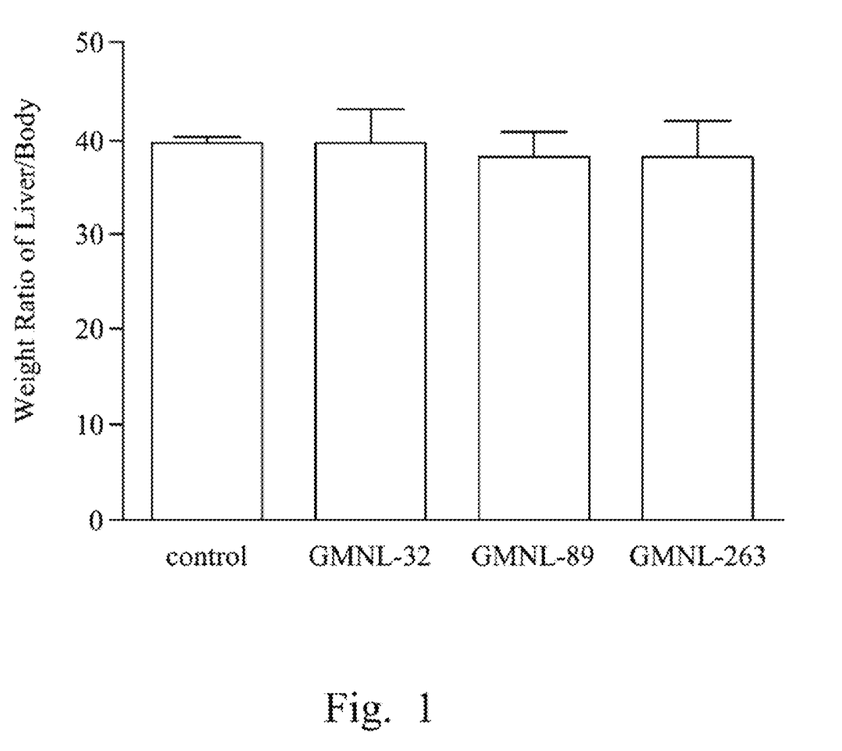
FIG. 1 depicts a histogram showing the liver-to-body weight ratios (L/B) of SLE mice according to several embodiments of the present invention.

Reference was made to TABLE 1 and FIG. 1. Table 1 shows the liver weight (g), the body weight (g), and the liver-to-body weight ratios (L/B) of the SLE mice. FIG. 1 is a histogram showing the liver-to-body weight ratios (L/B) of the SLE mice according to an embodiment of the present invention. In Table 1 and FIG. 1, p is smaller than 0.05 ($p<0.05$).

As shown in the results of Table 1 and FIG. 1, the liver-to-body weight ratios (L/B) of the SLE mice in the experimental groups (fed *L. paracasei* strain GMNL-32, *L. reuteri* strain GMNL-89, and *L. reuteri* strain GMNL-263) did not have significant differences compared to the SLE mice of the control group (fed with deionized water). Therefore, this result indicated that the SLE mice fed various *Lactobacillus* strains did not have significant influence on the liver weight and the body weight.

Figure 3A:
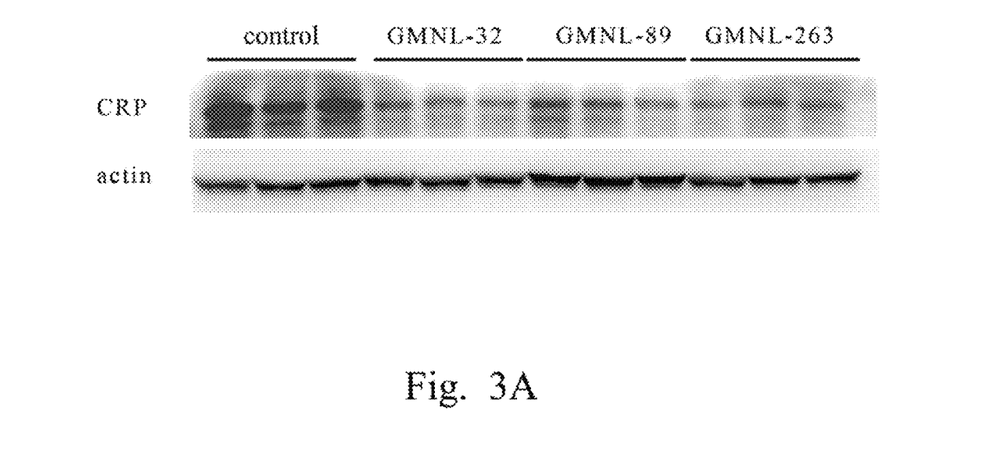
Figure 3B:
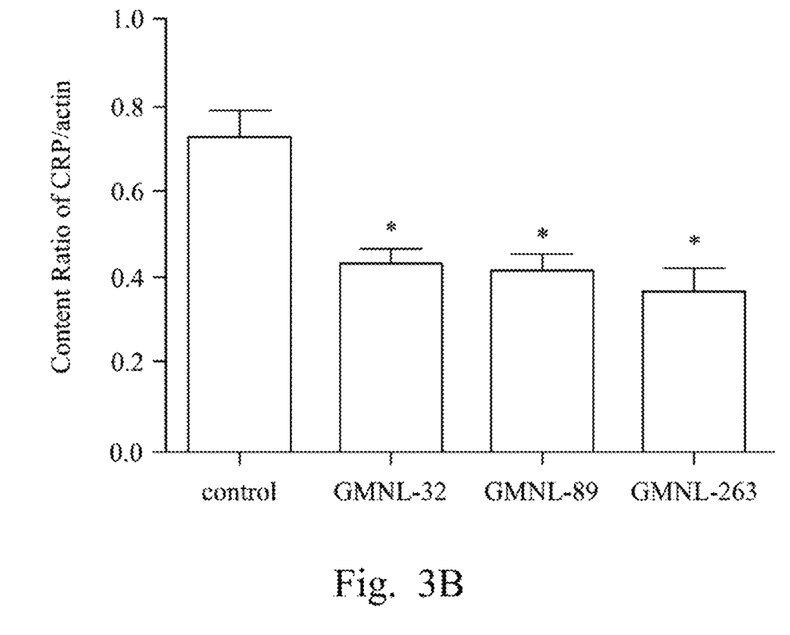
Figure 4A:
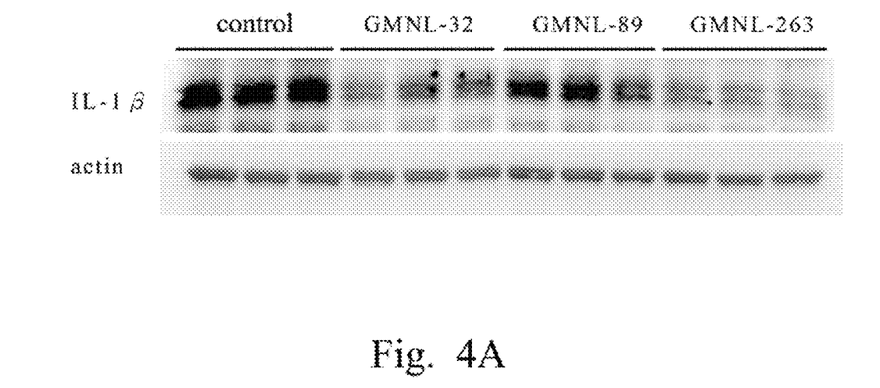
Figure 4B:
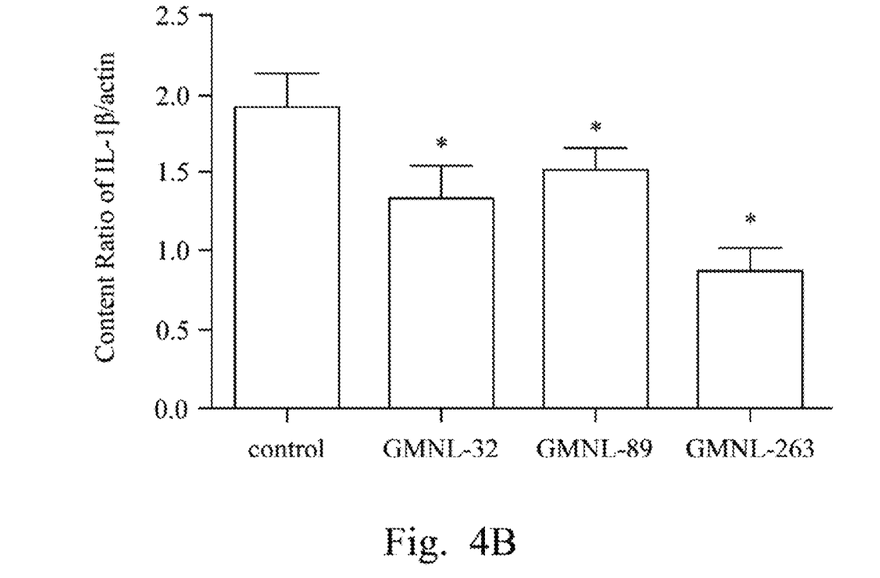
Figure 5A:
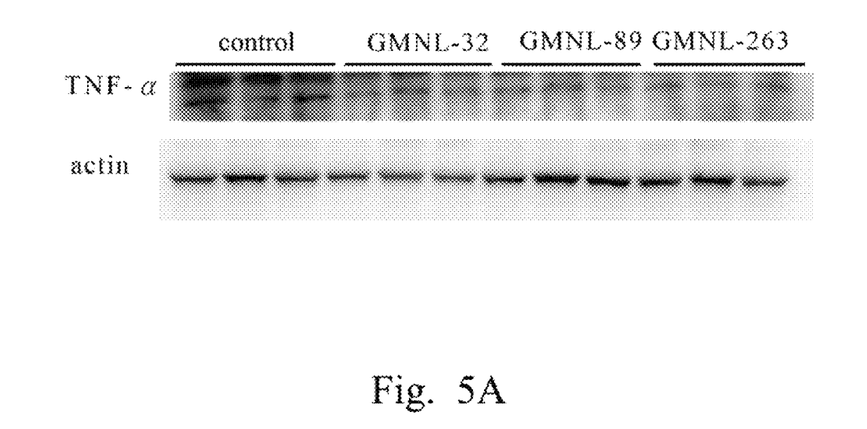
Figure 5B:
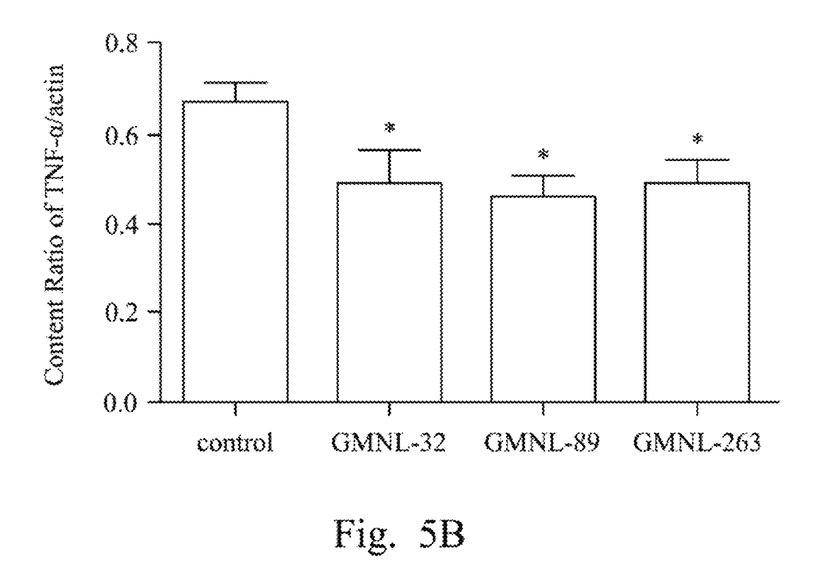
Figure 6A:
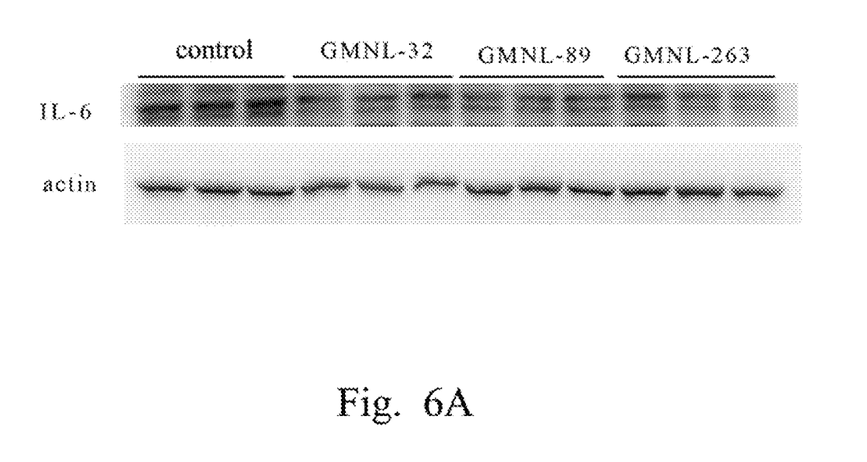
Figure 6B:
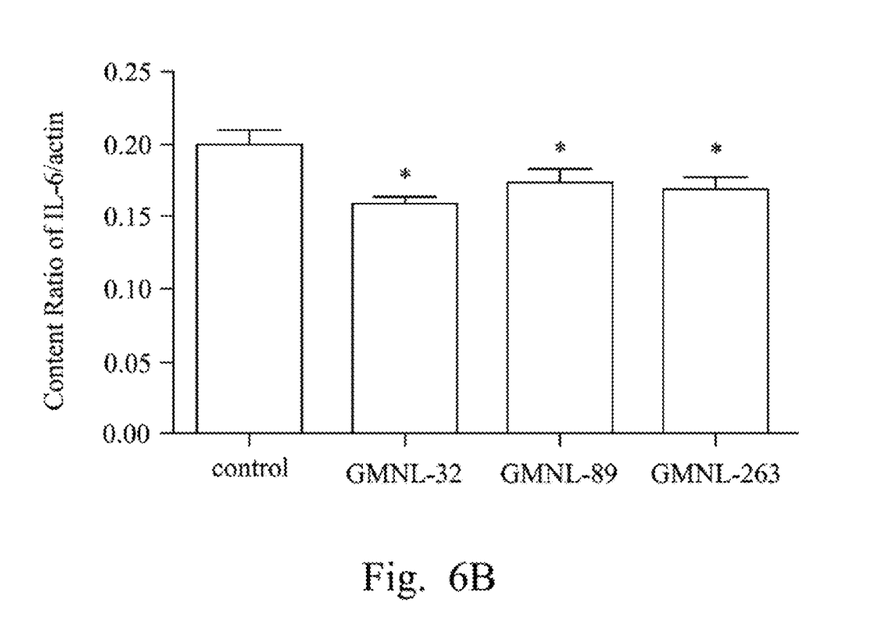
Figure 7A:
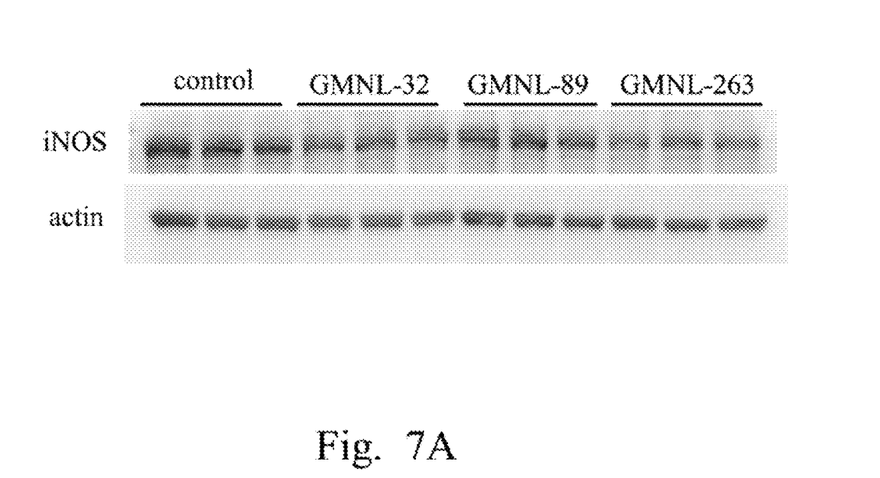
Figure 7B:
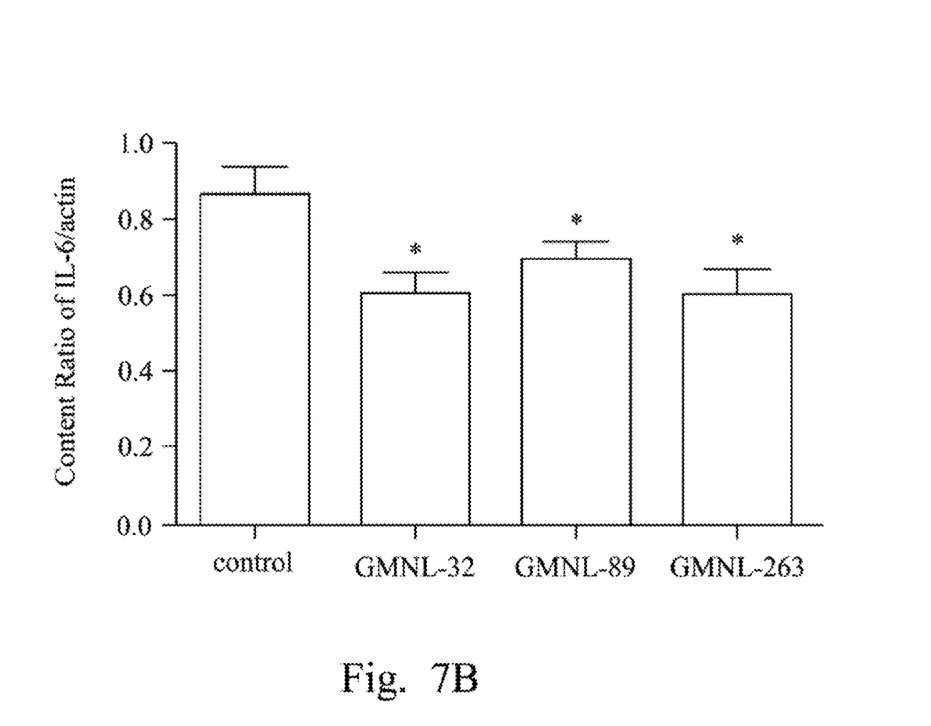
Figure 8A:
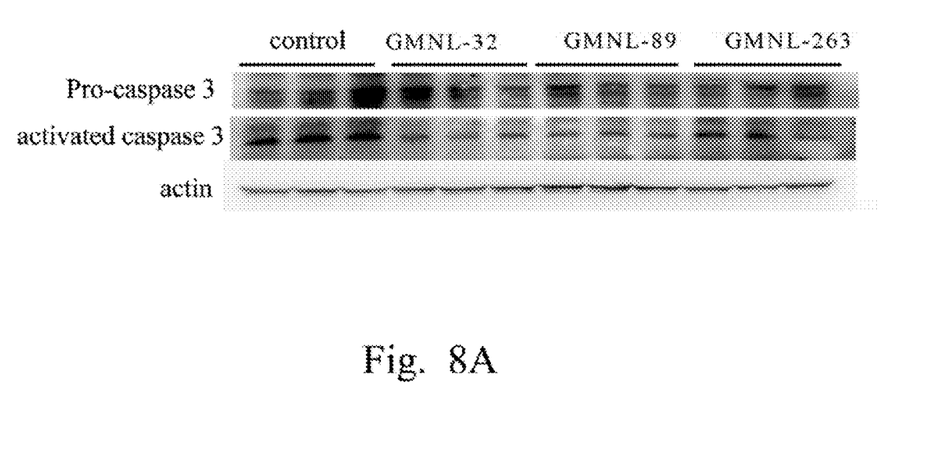

2. Evaluation of the Influence of the LAB Strains on the Expression of MMP-9, CRP, IL-1β, TNF-α, IL-6, iNOS and Caspase-3 in Liver Tissue of SLE Animal Reference was made to FIGS. 2A, 3A, 4A, 5A, 6A, 7A, and 8A, which were images respectively showing the results of gelatin-SDS-PAGE gel electrophoresis of MMP-9 (FIG. 2A), and the western blotting analyses of CRP (FIG. 3A), IL-1β (FIG. 4A), TNF-α (FIG. 5A), IL-6 (FIG. 6A), iNOS (FIG. 7A) and caspase-3 (FIG. 8A) of liver tissue of SLE mice according to several embodiments of the present invention.

Figure 2A:
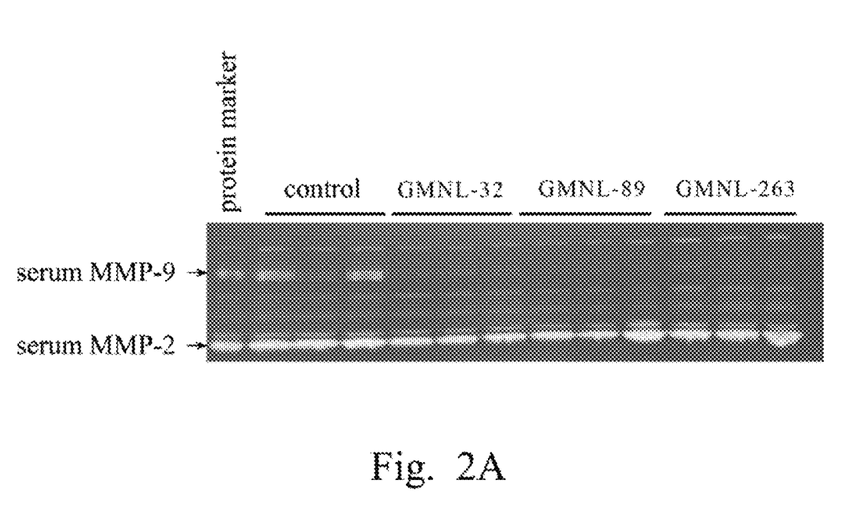
FIGS. 2A, 3A, 4A, 5A, 6A, 7A, and 8A are images respectively showing the results of gelatin-SDS-PAGE gel electrophoresis of MMP-9 (FIG. 2A), and the western blotting analyses of CRP (FIG. 3A), IL-1β (FIG. 4A), TNF-α (FIG. 5A), IL-6 (FIG. 6A), iNOS (FIG. 7A) and caspase-3 (FIG. 8A) of liver tissue of SLE mice according to several embodiments of the present invention.
Figure 2B:
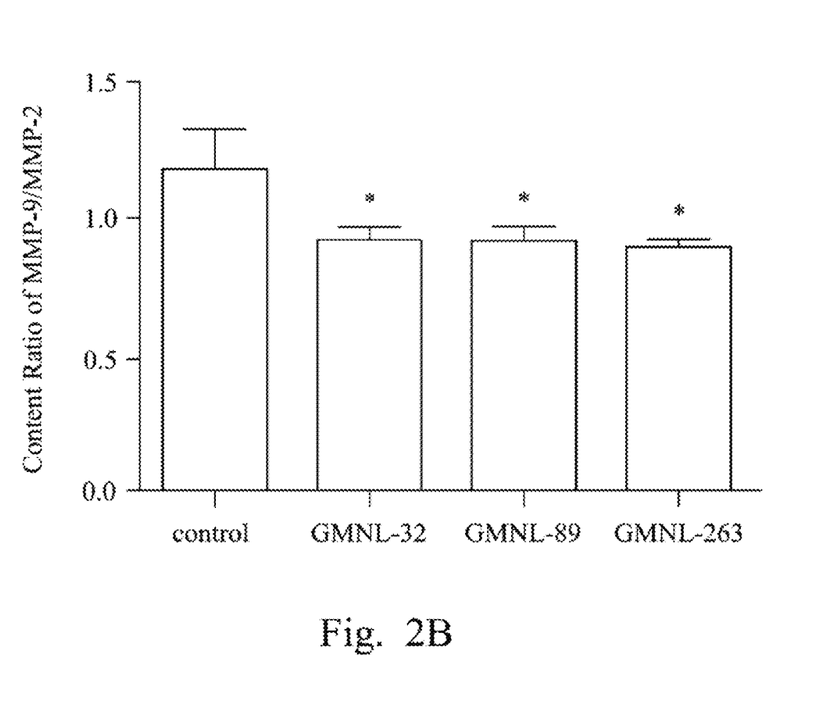
FIGS. 2B, 3B, 4B, 5B, 6B, 7B, and 8B are histograms respectively showing the content ratios of MMP-9/MMP-2 (FIG. 2B), CRP/actin (FIG. 3B), IL-1β/actin (FIG. 4B), TNF-α/actin (FIG. 5B), IL-6/actin (FIG. 6B), iNOS/actin (FIG. 7B) and caspase-3/actin (FIG. 8B).

In FIG. 2A, the first lane referred to the commercial protein marker, the second to the fourth lanes referred to the control group, the fifth to the seventh lanes referred to the experimental group fed with *L. paracasei* strain GMNL-32, the eighth to the tenth lanes referred to the experimental group fed with *L. reuteri* strain GMNL-89, and the eleventh to the thirteenth lanes referred to the experimental group fed with *L. reuteri* strain GMNL-263. The expression of MMP-2 was used as the internal control.

In FIGS. 3A to 8A, the first lane referred to the commercial protein marker, the second to the fourth lanes referred to the control group, the fifth to the seventh lanes referred to the experimental group fed with the *L. paracasei* strain GMNL-32, the eighth to the tenth lanes referred to the experimental group fed with *L. reuteri* strain GMNL-89, and the eleventh to the thirteenth lanes referred to the experimental group fed with *L. reuteri* strain GMNL-263. The expression of actin was used as the internal control.

Figure 8B:
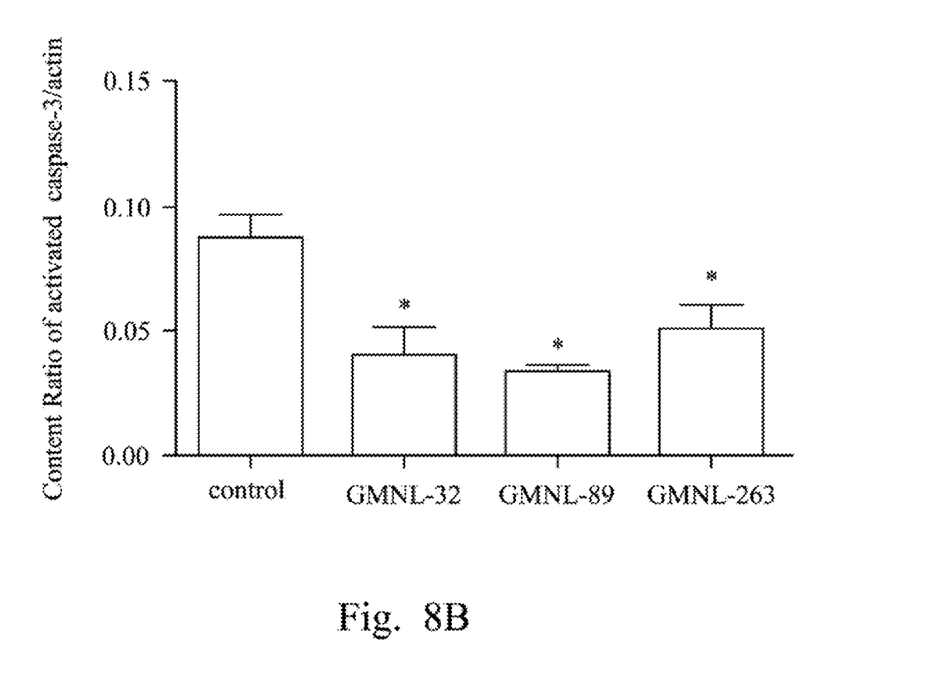

In addition, reference was made to FIGS. 2B, 3B, 4B, 5B, 6B, 7B, and 8B, which were histograms respectively showing the content ratios of MMP-9/MMP-2 (FIG. 2B), CRP/actin (FIG. 3B), IL-1β/actin (FIG. 4B), TNF-α/actin (FIG. 5B), IL-6/actin (FIG. 6B), iNOS/actin (FIG. 7B) and caspase-3/actin (FIG. 8B).

As shown in the results of FIG. 2A to FIG. 8B, it was found that, compared to the SLE mice feeding deionized water, the indicators of liver inflammation (for example, serum MMP-9, CRP, IL-1β, TNF-α and IL-6) and apoptosis (for example, caspase-3) can be effectively reduced in SLE mice of the experimental groups feeding *L. paracasei* strain GMNL-32, *L. reuteri* strain GMNL-89 and *L. reuteri* strain GMNL-263.

Example 3: Evaluation of the Efficacy of the LAB Strains to CD4$^+$/CD25$^+$ Splenic Regulatory T (Treg) Cell The spleens of the SLE mice in the EXAMPLE 1 were cut into small pieces, immersed in HBSS solution (1 g/10 mL) and deoxyribonuclease I (Life Technologies, Inc., U.S.A.) and incubated at 37° C. for 15 minutes. The HBSS solution included 0.05 mg/mL of collagenase type I, 0.05 mg/ml of collagenase type IV, 0.025 mg/ml of hyauronidase and 1 mg/ml of soybean trypsin inhibitor (Life Technologies, Inc., U.S.A.). Next, cells were collected by centrifugation, resuspended in HBSS digestion solution and incubated at 37° C. for 15 minutes. Undigested tissue pieces were filtered and removed, remaining splenocytes were washed by RPMI 1640 medium. Afterwards, splenocytes were separated by Ficoll-Paque gradient and dead cells were removed.

The resultant splenocytes were analyzed. The splenocytes were labeled by direct conjugated antibodies, including fluorescein isothiocyanate (FITC)-conjugated anti-CD4$^+$ monoclonal antibody, and FITC-conjugated anti-CD25$^+$ monoclonal antibody (BioLegen Inc., CA, U.S.A.). After the surface labeling, the splenocytes were fixed according to the manufacturer's instructions, the fluorescence intensities of the splenocytes were analyzed by flow cytometer (Becton Dickinson, Mountain View, Calif., U.S.A.), and the result was shown in FIG. 9.

Figure 9:
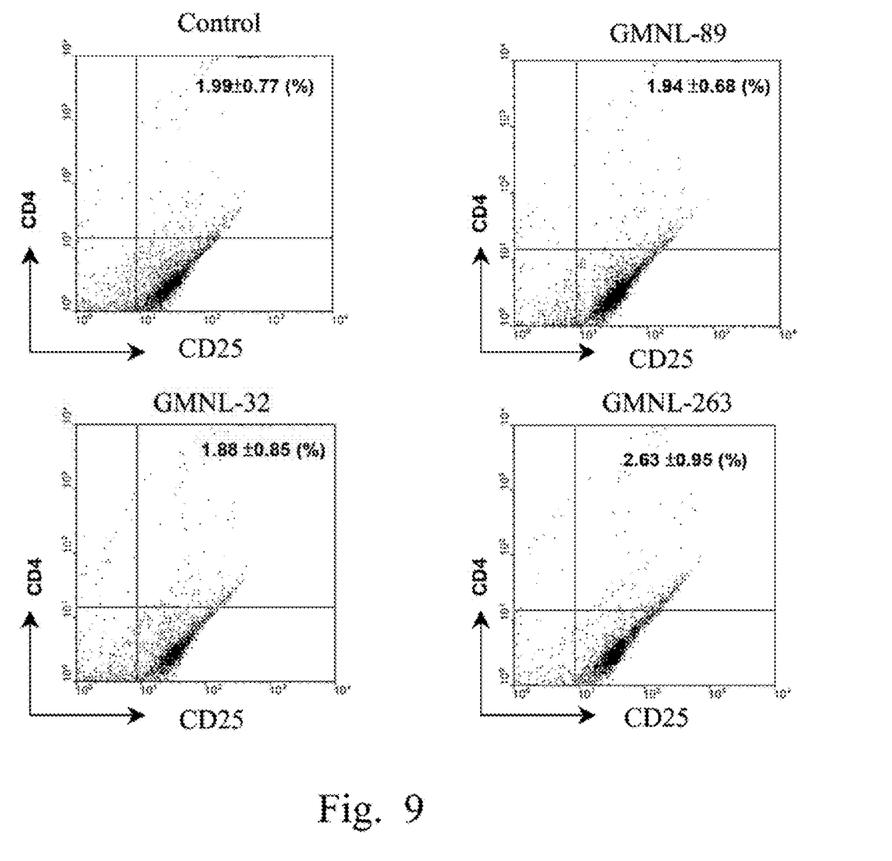
FIG. 9 shows the result of flow cytometry analysis of $CD4^+/CD25^+$ splenic Treg cells of SLE mice according to several embodiments of the present invention.

Reference was made to FIG. 9, which showed the result of flow cytometry analysis of CD4$^+$/CD25$^+$ splenic Treg cells of SLE mice according to several embodiments of the present invention. In FIG. 9, the left upper square showed the result of the control group, the left lower square showed the result of the experiment fed the *L. paracasei* strain GMNL-32, the right upper square showed the result of the experiment fed the *L. reuteri* strain GMNL-89, and the right lower square showed the result of the experiment fed the *L reuteri* strain GMNL-263.

As shown in the result of FIG. 9, it was found that the SLE mice fed the *L. reuteri* strain GMNL-263 effectively increased the ratio of CD4+/CD25+ splenic Treg cells.

Example 4: Evaluation of the Influence of the LAB Strains to the Heart Weight of SLE Animal 1. Evaluating the Influence of the LAB Strains on the Heart Weight of SLE Animal SLE mice of EXAMPLE 1 were respectively fed deionized water (the control group), the *L. paracasei* strain GMNL-32, the *L. reuteri* strain GMNL-89 and the *L. reuteri* strain GMNL-263. After 12 weeks, the heart weight, left ventricular weight, body weight, and tibial length were listed in TABLE 2 as follows.

TABLE 2

| | Group | | | |
|---|---|---|---|---|
| | Control | *L. paracasei* strain GMNL-32 | *L. reuteri* strain GMNL-89 | *L. reuteri* strain GMNL-263 |
| Body weight (g) | 38.84 ± 1.24 | 42.02 ± 3.53 | 42.11 ± 1.60 | 42.47 ± 0.65* |
| Heart weight (g) | 0.137 ± 0.006 | 0.176 ± 0.020* | 0.151 ± 0.010 | 0.143 ± 0.003 |
| Left ventricular weight (g) | 0.096 ± 0.0007 | 0.129 ± 0.016* | 0.109 ± 0.009 | 0.105 ± 0.003 |
| Heart weight/body weight ($\times 10^4$) | 35.42 ± 0.0002 | 42.51 ± 0.0009 | 35.95 ± 0.0003 | 33.74 ± 0.0001 |
| Left ventricular weight/body weight ($\times 10^4$) | 24.81 ± 0.0002 | 31.06 ± 0.0007 | 25.92 ± 0.0003 | 24.78 ± 0.0003 |
| Left ventricular weight/heart weight | 0.700 ± 0.020 | 0.729 ± 0.016 | 0.720 ± 0.021 | 0.735 ± 0.037 |
| Heart weight/tibial length (g/mm, $\times 10^4$) | 71.56 ± 0.0003 | 89.80 ± 0.0011* | 78.62 ± 0.0005 | 75.04 ± 0.0003 |
| Left ventricular weight/tibial length (g/mm, $\times 10^4$) | 50.11 ± 0.0003 | 65.55 ± 0.0009* | 56.65 ± 0.0005 | 55.10 ± 0.0001 |

As shown in the results of the Table 2, it was found that, compared to the SLE mice of the control group, the heart weight, left ventricular weight, and body weight, and the tibial length of SLE mice fed the *L. paracasei* strain GMNL-32, the *L. reuteri* strain GMNL-89 and the *L. reuteri* strain GMNL-263 were increased.

Figure 10A:
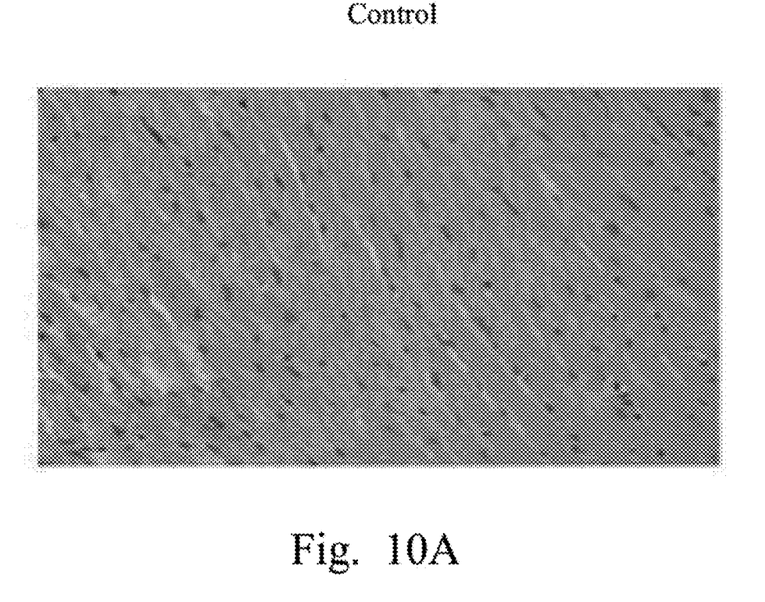
FIGS. 10A to 10D are images of cardiac tissue sections of SLE mice analyzed by Masson's trichrome staining according to several embodiments of the present invention.
Figure 10B:
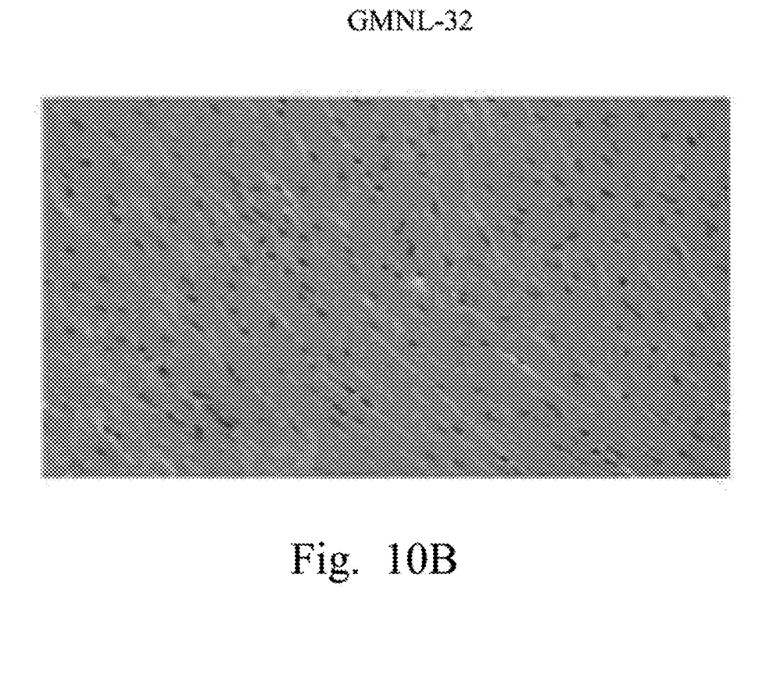
Figure 10C:
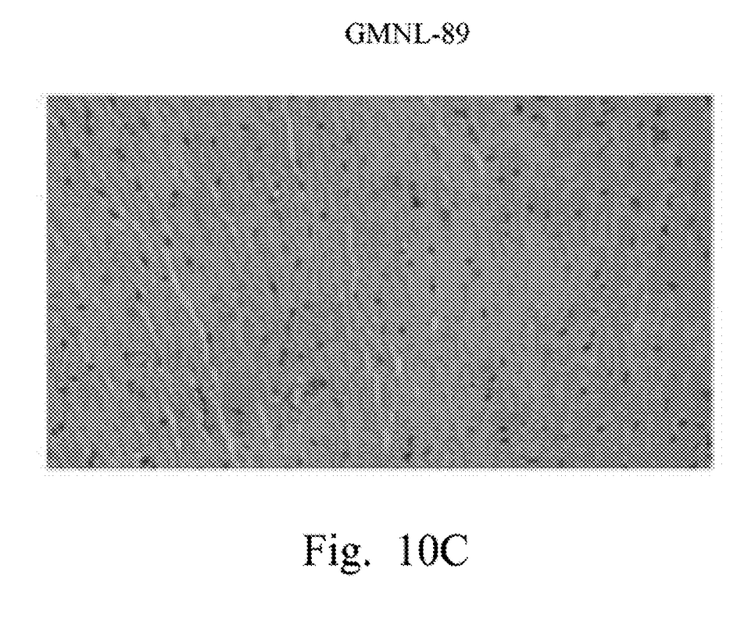
Figure 10D:
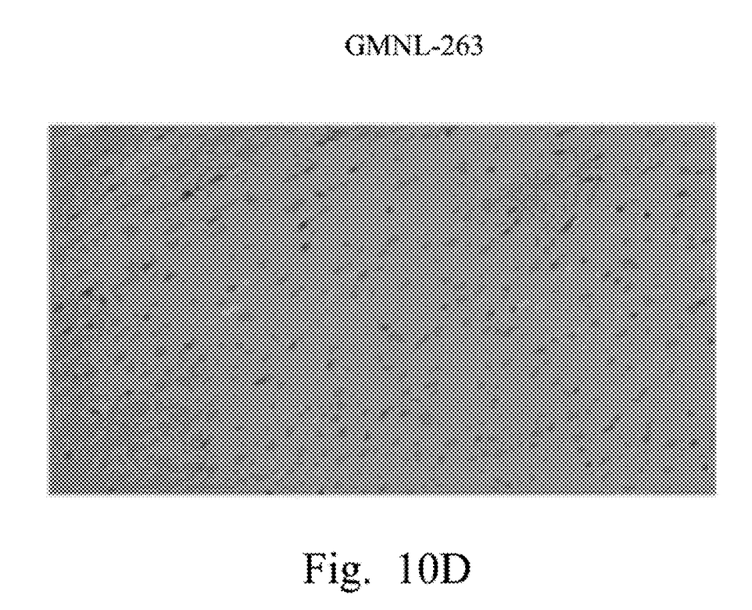

2. Evaluating the Influence of the LAB strains on the Cardiac Tissue. Cell Morphology and Cellular Structure of SLE Animal Reference was made to FIGS. 10A to 10D, which showed images of cardiac tissue sections of SLE mice analyzed by Masson's trichrome stain according to several embodiments of the present invention, which showed. FIG. 10A showed the image of the cardiac tissue section of SLE mice of the control group (FIG. 10A), the images of the cardiac tissue section of SLE mice of the experiment fed the *L. paracasei* strain GMNL-32 (FIG. 10B), the *L. reuteri* strain GMNL-89 (FIG. 10C) and the *L. reuteri* strain GMNL-263 (FIG. 10D).

As shown in the results of FIGS. 10A to 10D, it was found that, compared to the SLE mice fed with deionized water, the gap junctions between cardiac cells of the SLE mice fed *L. paracasei* strain GMNL-32, *L. reuteri* strain GMNL-89, and *L. reuteri* strain GMNL-263 were decreased.

It is necessarily supplemented that, specific strains, specific analysis methods, or specific equipments are employed as exemplary embodiments for clarifying the LAB strains used for preparation of a medical composition for treating cardiac and hepatic disease of the autoimmune disease of the present invention. However, as is understood by a person skilled in the art, other analysis methods or other equipments can be also employed in the LAB strains used for preparation of a medical composition for treating cardiac and hepatic disease of the autoimmune disease of the present invention, rather than limiting to thereto.

According to the embodiments of the present invention, the aforementioned isolated strain of *Lactobacillus* species, the medical composition containing the same, and the LAB-containing composition for treating the cardiac and hepatic disease of the autoimmune disease, the LAB strains themselves advantageously have multiple beneficial functions without side effects. Such medical composition is easy-to-use in the daily life of patients via oral administration, and can treat, alleviate, control, improve, and/or prevent the related complications (cardiac and hepatic disease) caused by the autoimmune disease (such as SLE), thereby developing other application fields of the LAB strains.

Although the present invention has been described in considerable detail with reference to certain embodiments thereof, other embodiments are possible. Therefore, the spirit and scope of the appended claims should not be limited to the description of the embodiments contained herein.

What is claimed is:

1. A method of treating a cardiac or hepatic disease caused by systemic lupus erythematosus, comprising orally administering a lactic acid bacteria (LAB)-containing composition to an individual, wherein the LAB-containing composition comprises an effective amount of a LAB strain and a pharmaceutically acceptable carrier, the effective amount is $1 \times 10^9$ CFU/g per individual, the individual is a mouse, and the LAB strain is *Lactobacillus reuteri* strain GMNL-263, CCTCC M209263, for reducing gap junctions between cardiac cells or inhibiting activities of matrix metallopeptidase 9 (MMP-9), C-reactive protein (CRP), interleukin-1β (IL-1β), tumor necrosis factor-α (TNF-α), IL-6, inducible NO synthase (iNOS) and caspase-3 of a hepatocyte.

2. The method of claim 1, wherein the LAB strain inhibits activities of matrix metallopeptidase 9 (MMP-9), C-reactive protein (CRP), interleukin-1β (IL-1β), tumor necrosis factor-α (TNF-α), IL-6, inducible NO synthase (iNOS) and caspase-3 of a hepatocyte.

3. The method of claim 1, wherein the LAB strain reduces gap junctions between cardiac cells.

* * * * *